(12) United States Patent
Van Der Pol

(10) Patent No.: US 12,310,633 B2
(45) Date of Patent: May 27, 2025

(54) CONNECTOR FOR SPINAL COLUMN SUPPORT

(71) Applicant: SIGNUS MEDIZINTECHNIK GMBH, Alzenau (DE)

(72) Inventor: Bas Van Der Pol, Alzenau (DE)

(73) Assignee: SIGNUS MEDIZINTECHNIK GMBH, Alzenau (DE)

( * ) Notice: Subject to any disclaimer, the term of this patent is extended or adjusted under 35 U.S.C. 154(b) by 287 days.

(21) Appl. No.: 17/628,820

(22) PCT Filed: Jul. 27, 2020

(86) PCT No.: PCT/EP2020/071154
§ 371 (c)(1),
(2) Date: Jan. 20, 2022

(87) PCT Pub. No.: WO2021/018846
PCT Pub. Date: Feb. 4, 2021

(65) Prior Publication Data
US 2022/0257291 A1    Aug. 18, 2022

(30) Foreign Application Priority Data
Jul. 30, 2019 (DE) .................. 10 2019 005 376.1

(51) Int. Cl.
*A61B 17/70* (2006.01)
(52) U.S. Cl.
CPC ................. *A61B 17/7049* (2013.01)
(58) Field of Classification Search
CPC ..................... A61B 17/7049–7053
See application file for complete search history.

(56) References Cited

U.S. PATENT DOCUMENTS 5,702,393 A * 12/1997 Pfaifer ............... A61B 17/7049
606/328
6,368,320 B1 * 4/2002 Le Couedic ....... A61B 17/7049
606/246

(Continued)

FOREIGN PATENT DOCUMENTS

| EP | 2480149 B1 | 5/2017 |
| EP | 2581057 B1 | 8/2017 |
| WO | 2009015100 A2 | 1/2009 |

OTHER PUBLICATIONS

English Translation of International Preliminary Report on Patentability Dated Feb. 1, 2022, 7 Pages.

*Primary Examiner* — Eduardo C Robert
*Assistant Examiner* — Steven J Cotroneo
(74) *Attorney, Agent, or Firm* — LUCAS & MERCANTI, LLP; Klaus P. Stoffel

(57) ABSTRACT

A connector for connecting two supporting rods of a spinal column supporting device, which rods are placed or are to be placed along a portion of spinal column. The connector includes a transverse rod, a first coupling that couples the transverse rod to a first one of the supporting rods and a second coupling that couples the transverse rod to the second one of the supporting rods. At least one of the couplings has a clamping region that clamps the supporting rod with a clamping force and a force application component for generating an axial force that produces the clamping force, in particular in the form of an axial tensioning screw, the axial force being caused by screwing in of the screw, and the axial force being directed through the transverse rod.

16 Claims, 3 Drawing Sheets

(56) References Cited

U.S. PATENT DOCUMENTS

| | | | |
|---|---|---|---|
| 7,666,210 B2 * | 2/2010 | Franck | A61B 17/7052 606/250 |
| 8,262,700 B2 * | 9/2012 | Cho | A61B 17/7049 606/250 |
| 8,864,799 B2 | 10/2014 | Kraus | |
| 10,398,454 B2 * | 9/2019 | Patrinicola | A61B 17/7052 |
| 11,076,890 B2 * | 8/2021 | Ortiz | A61B 17/7083 |
| 2007/0049932 A1 | 3/2007 | Richelsoph | |
| 2008/0306538 A1 * | 12/2008 | Moore | A61B 17/7052 606/250 |
| 2012/0109202 A1 * | 5/2012 | Kretzer | A61B 17/7049 606/248 |
| 2012/0232593 A1 * | 9/2012 | Predick | A61B 17/7049 606/276 |
| 2013/0338721 A1 * | 12/2013 | Biedermann | A61B 17/7034 606/305 |
| 2014/0277163 A1 | 9/2014 | Kretzer | |
| 2015/0374414 A1 * | 12/2015 | Dant | A61B 17/7049 606/250 |

* cited by examiner

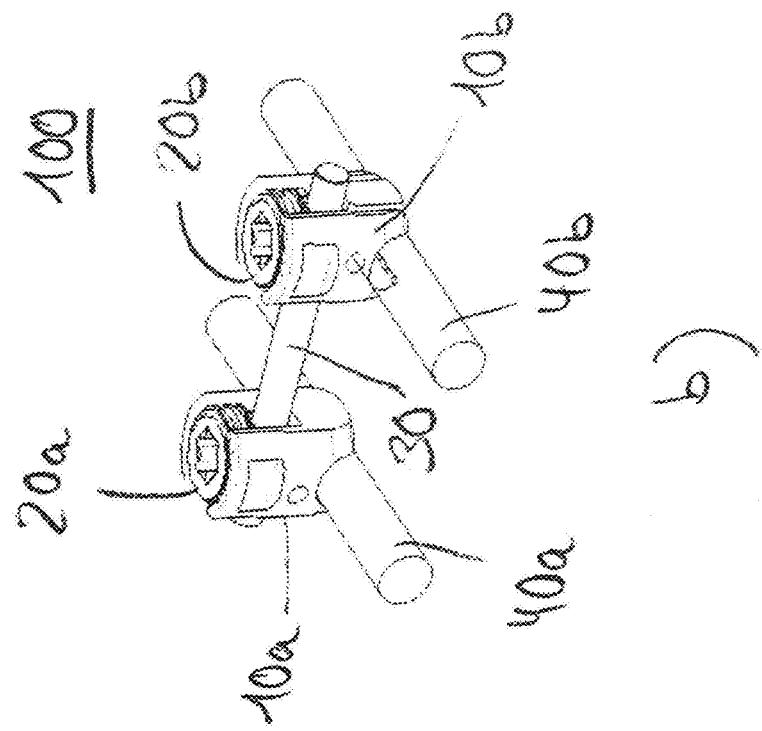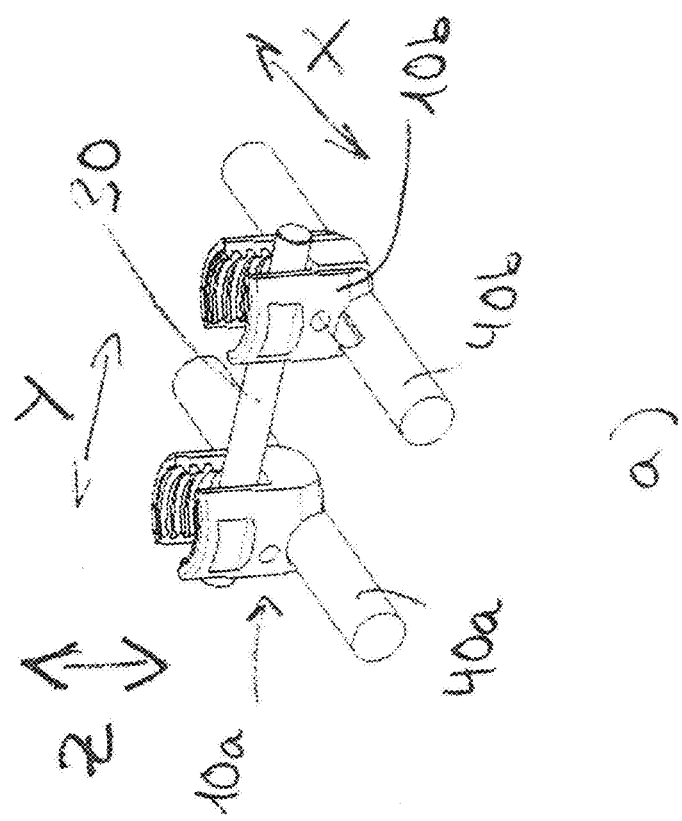
Fig. 2

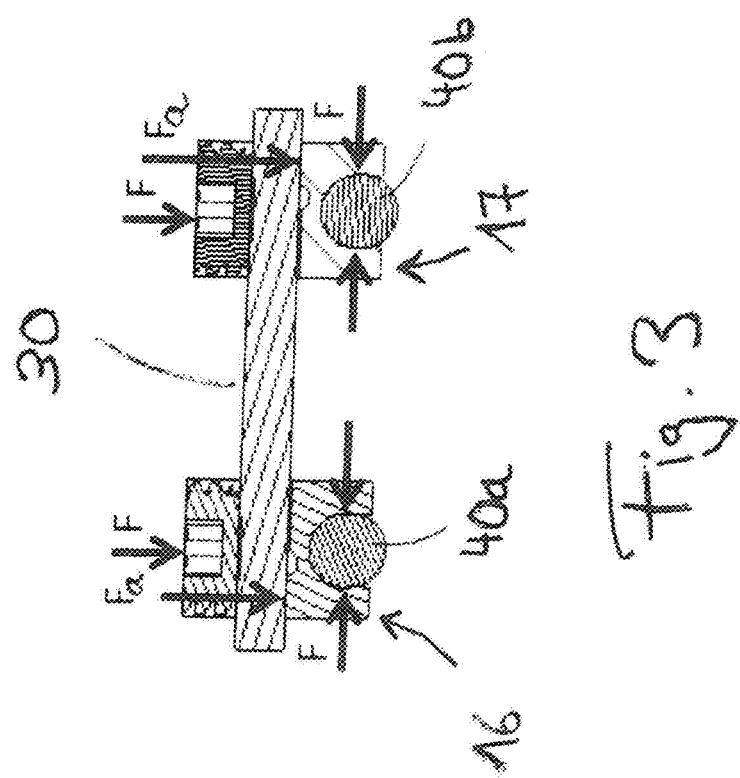

CONNECTOR FOR SPINAL COLUMN SUPPORT

CROSS-REFERENCE TO RELATED APPLICATIONS

The present application is a 371 of International application PCT/EP2020/071154, filed Jul. 27, 2020, which claims priority of DE 10 2019 005 376.1 filed Jul. 30, 2019, the priority of these applications is hereby claimed and the applications are incorporated herein by reference.

BACKGROUND OF THE INVENTION

The invention relates to a connector for connecting two support rods of a spinal column support device, which support rods are placed or are to be placed along a spinal column portion, comprising a transverse rod, a first coupling that couples the transverse rod to a first one of the support rods and a second coupling that couples the transverse rod to the second one of the support rods, wherein at least one of the couplings has a clamping region which clamps the support rod with a clamping force, and has force application means for generating an axial force that brings about the clamping force, the force application means being in the form of an axial clamping screw in particular and the axial force being caused by screwing in said clamping screw.

Such connectors are well known, for example from US 2007/004932 A1. In the connectors taught therein, not only does screwing in the clamping screw bring about the clamping force that clamps the support rod, but the clamping screw is also surrounded by an expansion sleeve which spreads radially during the screwing-in process and thereby likewise clamps the transverse rod in a transverse rod groove.

SUMMARY OF THE INVENTION

The invention is based on the object of developing a connector of the type set forth at the outset, in particular in view of a satisfactory combination of simple structure of the connector and simple handling thereof.

This object is achieved by the invention by way of a development of the connector of the type set forth at the outset, which is essentially characterized in that the axial force is guided through the transverse rod. Therefore, the transverse rod is part of the force transmission path, along which clamping by way of the application of force or establishing a rigid coupling between connector rod and transverse rod is brought about, for instance from screwing in to tightening the clamping screw.

This simplifies the handling and the connector makes do with fewer components.

Further preferred embodiments and aspects of the invention are specified in the dependent claims.

Thus, preferably, a first part of the clamping region has a resilient arm. In this context, the clamping region can be able to be clipped onto the support rod by virtue of the resilient arm yielding and pressing back to its original position on account of its resilient mount. It is understood that clipping on is preferably possible by hand and without tools.

Preferably, the clamping region is formed in one piece and, in particular, formed in one piece with the coupling except for the force application means (e.g., a clamping screw). Here, provision is particularly preferably made for a resilient mount of the resilient arm to be facilitated by a material weakening of the coupling. By way of example, the latter can be formed by a bore that goes through the body of the coupling. This simplifies the production with regards to as few components as possible.

In a particularly preferred embodiment, a rest for the transverse rod that is formed on the side of the transverse rod distant from the clamping screw is located axially at a higher level in the region of the resilient arm than in any other part of the clamping region when no axial force is applied. In this way, it is particularly simple to apply force to the resilient arm. As a result of the application of force, the resilient effect of the arm is canceled, and a clamping force that acts radially on the transverse rod and is sufficient to bring about rigid coupling is caused in the case of a sufficient axial force. To this end, the clamping faces of the clamping region that face the support rod have a design that is at least partly complementary to the contour of the support rod, when seen in the cross section.

The resilient mount, in particular the material weakening bringing about the latter, can be localized asymmetrically in relation to the clamping screw, preferably to the side of the resilient arm, when seen in the axial section. This makes it easier to match the deformation paths and avoids overlong deformation paths at the free end of the resilient arm.

The connector can preferably adopt a plurality of states, for instance a state in which the transverse rod is already held in the couplings but an axial displaceability along the transverse rod for the purposes of setting a positioning distance still is possible, a state in which the positioning distance has been set securely and radial coupling to the support rods has already been established but a displacement along the support rods still is possible, and also the ultimately sought-after final state of rigid coupling of the two support rods to one another by way of the connector. In the simplest realization of the force application means, the latter state is achieved by tightening a clamping screw, the earlier states corresponding to states of a shallower screw-in depth of, or of less application of torque to, the clamping screw.

The couplings may have a similar to identical embodiment (nevertheless, a non-identical design is possible during assembly, for example by virtue of the respective resilient arms of the couplings facing away from one another). In a very simple design, the connector may consist of a total of only five components and a total of three different components (two identical receptacles, two identical clamping screws and the transverse rod). However, provision could also be made for the transverse rod and the other coupling to already be securely connected to one another and to be fastened as one component, for example by way of a groove and locking screws on a support rod that has been placed into said groove.

In a preferred embodiment, the two couplings each have a receptacle which, in the axial direction, has a recess at its upper side, a receptacle space in the form of a continuous groove in the transverse direction being formed at the lower end region of said recess. Further preferably, side regions extending along the recess in the axial direction have a thread on their inner side, the axial clamping screw interacting with said thread.

However, the invention also provides assortments, for example with transverse rods of different lengths, or else couplings designed for coupling to support rods with different diameters.

Consequently, the connector is suitable for spinal column supports to be newly implanted and also, as additional transverse stiffening, suitable for already existing spinal column supports (in the case of which there may be different transverse dimensions of the support rods depending on the patient and system manufacturer, or depending on the requirements of the implantation at that time).

The invention also protects a coupling of such a connector as such, and also the preparation of such a connector for its upcoming use in the creation of a transverse connection between two support rods of a spinal column support device. This may contain a plurality of aspects, firstly the embodiment (provided in any case) of the connector from biocompatible materials (for instance titanium, stainless steel or else plastics, for instance biocompatible polymers which are known to a person skilled in the art from the field of implantology) from a materials point of view, and the obvious preparation by disinfection steps such as, e.g., autoclaving, the suitable assembly which matches support rods of the spinal column support device and/or the ready-to use provision of the assembled parts for the surgeon carrying out the implantation.

Moreover, the invention also protects entire spinal column support devices having such connectors. In this case, the spinal column support devices may also comprise attachment mechanisms for the support rods in addition to the support rods, for instance pedicle screws of any design and the coupling mechanisms thereof, via connection elements, to the support rod rigidly connecting the plurality of pedicle screws, said connection elements for example allowing polyaxial adjustments (fixed coupling with a polyaxially formable angle arrangement of the pedicle screw with respect to the support rod).

In a simple configuration where the assumption of approximately parallel support rods to be connected is made, the direction of extent thereof, the direction of extent of the course of the transverse rod and the axial force (axial introduction direction of the clamping screws) can define a Cartesian coordinate system, it however being understood that non-orthogonal transverse positions are also possible, as are adjustable angle arrangements although the latter may increase the minimum number of components required.

BRIEF DESCRIPTION OF THE DRAWING

Further features, details and advantages of the invention arise from the following description with reference to the attached drawing, in which FIG. 1a shows a front view with a direction of view in the connection direction, FIG. 1b shows a side view with a direction of view along the extent of the support rod, and FIG. 1c shows a sectional view orthogonal to the direction of view of FIG. 1b, FIG. 2 shows a connector, to be precise without clamping screws in FIG. 2a and with clamping screws in FIG. 2b, and FIG. 3 shows a sectional view of FIG. 2b, with force arrows being plotted.

DETAILED DESCRIPTION OF THE INVENTION

Figure 1:
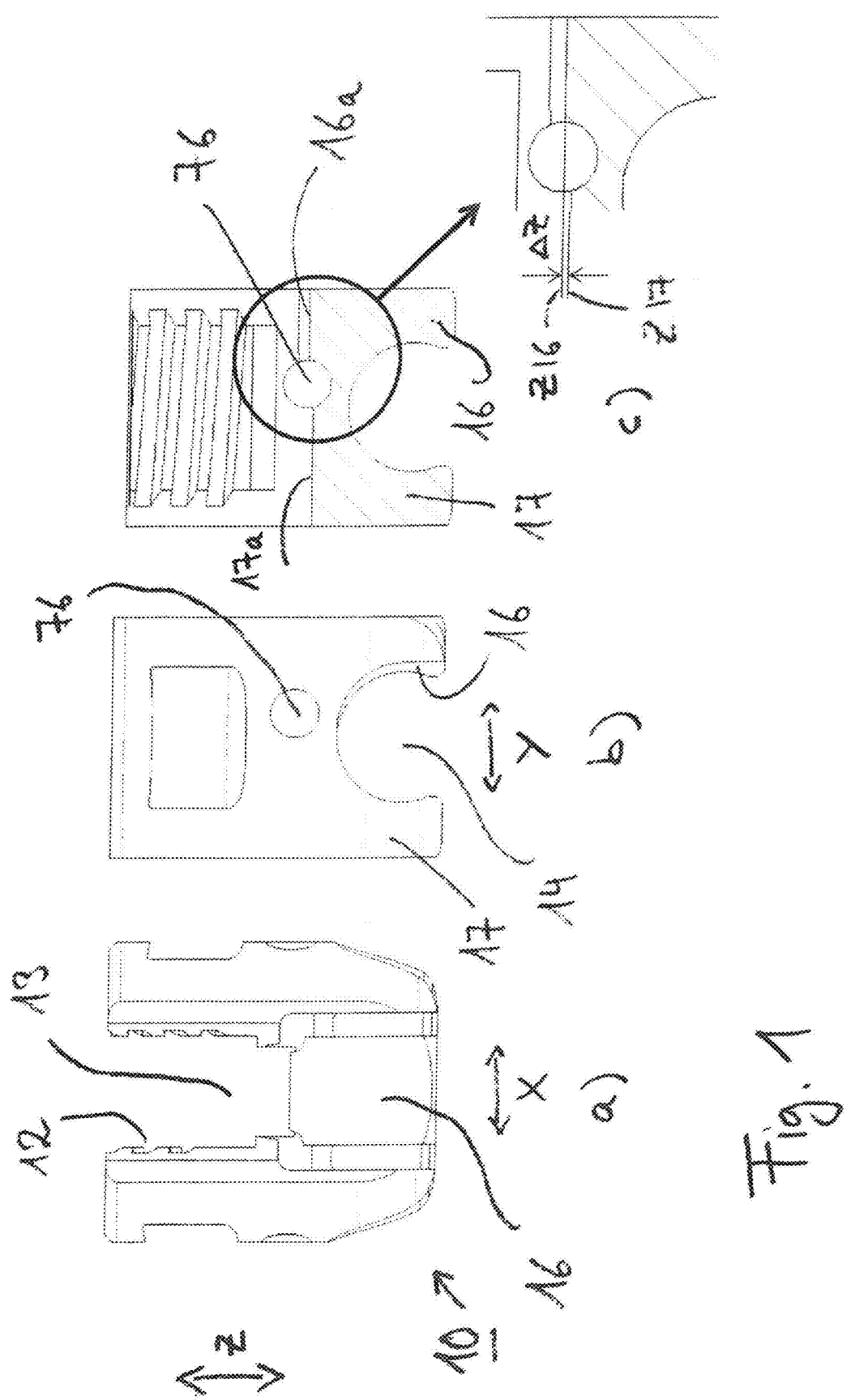
FIG. 1 shows a part of a coupling of a connector, to be precise

FIG. 1 illustrates a receptacle 10, which together with a clamping screw, which is not illustrated in FIG. 1 and which interacts with the thread 12 of the receptacle 10 and together with a transverse rod 30, in a respective double implementation, forms a connector 100 which is illustrated in interacting fashion in FIG. 2b and which interconnects two support rods 40a, 40b by way of transverse stiffening.

Even though this is not illustrated in FIG. 2b, the support rods 40a, 40b are parts of a spinal column support device and when implanted into the human body are rigidly connected via suitable couplings to pedicle screws that are screwed into vertebrae. Such spinal column support devices are known from the art and therefore not discussed in more detail; instead, reference is made to relevant systems in this regard, as are disclosed for example in WO 2009/015100 A2 and EP 2 581 057 B1, the documents respectively being incorporated by reference.

It is evident from the front view of FIG. 1a that in the axial direction Z the receptacle 10 has a recess on its upper side, a receptacle space in the form of a continuous groove in the Y-direction being formed at the lower end region of said recess. As is likewise evident from FIG. 1a and FIG. 2a, the transverse rod 30 can be introduced into the receptacle space from the top, along the recess and in the axial direction, the receptacle space for the transverse rod being formed at the lower end region of said recess. The side regions that extend along the recess in the axial direction bear the thread 12 on their inner sides. With the direction of view in the axial direction Z, the recess appears as a threaded bore, which is perforated by the groove 13 in the transverse direction Y.

A receptacle groove 14 which extends transversely to the groove 13—orthogonally in this exemplary embodiment—and which is better identifiable in FIG. 1b is formed in the lower region of the receptacle 10 in relation to the axial direction Z. This receptacle groove is designed to receive a support rod 40 (not illustrated in FIG. 1) and surround the latter over more than 180° in the circumferential direction. A resilient arm 16, which is arranged centrally in relation to the direction of extent of the direction of extent X of the support rod 40, together with a side holder 17 opposite said resilient arm forms a clamping region, in which the support rod 40 is clamped and ultimately securely fixed.

To this end, the constriction between the facing lower end portions of the side holder 17 and of the resilient arm 16 has an intervening space that is smaller, but only just smaller, than the diameter of the support rod 40 in a preferred embodiment. The clamping region 16, 17 can consequently be clipped onto the support rod 40, with the resilient arm 16 elastically deforming during the clip-on movement on account of its resilient mount. The resilient mount in the transition region to the side holder 17 is facilitated by a material weakening 76 in the form of a bore that traverses the receptacle 10 in the X-direction. Consequently, a material bridge remains between the lower edge of the bore 76 in FIG. 1c and the section of the boundary of the groove 14 lying opposite thereto.

Once the receptacle 10 has been clipped onto the rod 40, it can conversely also be removed from rod 40 again, unless the clamping force of the clamping region 16, 17 is so strong as a result of the effect of the force application means, formed by the clamping screw 20 in this exemplary embodiment, that lifting off in the radial direction is no longer possible.

It is clearly evident from FIG. 1c and its enlarged detail that the level Z16 of the upper face 16a of the resilient arm 16, which face forms a bearing face for the transverse rod 30, is higher than the level Z17 of the upper face of the side holder 17, which face likewise is a bearing face for the transverse rod 30, by height difference $\Delta Z$ in the axial direction Z in a state when no force is applied. Consequently, if the resilient arm 16 denotes the movable limb and the side holder 17 denotes the fixed limb of the clamping mechanism, realized here, under the application of axial force, the bearing face 16*a* of the movable limb is closer to the thread 12 than the bearing face of the fixed limb 17 in the axial direction Z.

If the clamping screw 30 is now screwed into the thread 12, the axial force caused thereby is guided through the transverse rod 30 and initially acts on the bearing face of the resilient arm 16, which is pressed axially downward as a result, and this is reflected in radial transverse forces, plotted in the Y-direction in FIG. 3, on account of the inner faces of the clamping region being complementary to the rod 40. In this case, the inner faces of the clamping region 16, 17 establish pressurized contact around the rod 40 over an angle region greater than 180°, preferably greater than 200°, and approximately 225° in the present embodiment.

It is understood that tightening of the clamping screw 20*a* (that is to say, exerting a torque that is above a specified critical threshold) ensures fixed rigid coupling of the support rod 40 with the receptacle 10. It is furthermore understood that, on account of the structural design of guiding the axial force through the transverse rod, the transverse rod 30 is also rigidly and securely coupled to the receptacle 10 in the process (this state is shown in FIGS. 2*b* and 3).

During use, the two receptacles 10*a*, 10*b* (FIG. 2*a*) of the connector 100 for example could be separately clipped onto the support rods 40*a*, 40*b* to be connected and as shown in FIG. 2*a* the transverse rod 30 could be introduced into the receptacles 10*a*, 10*b* until it comes to rest on the bearing faces 16*a* of the respective resilient arms 16 in the transverse rod channel 13. As an alternative to the design of FIG. 2, it would also be possible for the receptacles 10*a*, 10*b*, before these two receptacles are clipped on, to be coupled to one another by means of the transverse rod 30 and the clamping screws 20*a* by very slightly screwing in the clamping screws 20 so as to prevent slippage out of the channel 13 in the Z-direction so that the distance between the two couplings is only still adjustable by displacement along the Y-axis, and for this distance to be suitably adjusted in relation to the distance of the support rod 40*a*, 40*b* and be set by screwing the clamping screws 20*a*, 20*b* slightly further. In this state, the couplings that have already been connected to the transverse rod 30 can also be clipped together onto the respective support rods 40*a*, 40*b*.

Further screwing then prevents the couplings from being released from the support rods 40*a*, 40*b* but still permits a common displacement, undertaken along the direction of extent X thereof, for the appropriate setting of the final position, in which, at the right mutual distance and at the right level in respect of the extent of the spinal column, the connector is finally set to rigid coupling by tightening the clamping screws 20*a*, 20*b*.

As is evident from the aforementioned options, it is easy to manage the connection of the support rods 40*a*, 40*b* and the connector makes do with a few components.

It is likewise evident to a person skilled in the art that the structure of the receptacle 10 of the coupling is not restricted to that of the embodiment illustrated in exemplary fashion.

Rather, the individual features of the description above and of the claims below may be essential, either on their own or in any combination, for the implementation of the invention in its various embodiments.

The invention claimed is:

1. A connector for connecting two support rods of a spinal column support device, which support rods are configured to be placeable along a spinal column portion, the connector comprising:

a transverse rod;
a first coupling that couples the transverse rod to a first of the support rods; and
a second coupling that couples the transverse rod to a second of the support rods, wherein
at least one of the couplings has a clamping region that clamps the support rod with a clamping force, and has force applicator for generating an axial force that brings about the clamping force, the force applicator being an axial clamping screw and the axial force being caused by screwing in said clamping screw, wherein the axial force is guided through the transverse rod, wherein a resilient arm together with a side holder form the clamping region, wherein the side holder is opposite said resilient arm such that a clamping face facing the support rod from one lateral side is an inner face of the side holder and a clamping face facing the support rod from an opposite lateral side is an inner face of the resilient arm, said clamping region being formed in one piece and being clippable onto the support rod, and wherein a rest for the transverse rod that is formed on a side of the transverse rod distant from the clamping screw is located axially at a higher level in a region of the resilient arm than at said side holder when no axial force is applied, so that the axial force guided through the transverse rod initially acts on a bearing face of the resilient arm, said bearing face forming said rest for the transverse rod in the region of the resilient arm, wherein said at least one of the couplings has an upper side with a recess and a receptacle space formed as a continuous groove in a transverse direction, such that, in a state in which the clamping screw is not screwed into a threaded bore perforated by said continuous groove, the transverse rod is introducible into the receptacle space from above.

2. The connector according to claim 1, wherein the clamping region is configured to be clippable onto the support rod.

3. The connector according to claim 1, wherein the coupling has a material weakening that facilitates a resilient mount of the resilient arm.

4. The connector according to claim 3, wherein, as seen in an axial section, the material weakening has an asymmetric form in relation to the clamping screw.

5. The connector according to claim 1, having an adoptable first positioning state, in which the transverse rod is kept at a positioning distance from the support rods in the couplings by a preloaded state of the force applicator.

6. The connector according to claim 5, wherein the positioning state is adjustably variable.

7. The connector according to claim 5, having an adoptable securing state, in which the clamping force still allows movements of the coupling along the support rod but no longer allows said coupling to lift off from the support rod.

8. The connector according to claim 7, having an adoptable state of rigid coupling between the support and transverse rods, this state being brought about by a full application of the force applicator by tightening the clamping screw.

9. The connector according to claim 1, wherein both of the couplings have the clamping region and the force applicator.

10. The connector according to claim 9, wherein the first and second couplings are identical.

11. The connector according to claim 1, wherein at least one of: an axial direction that corresponds to an axis of the axial force runs orthogonal to a direction of extent of the transverse rod; the axial direction runs orthogonal to a direction of extent of at least one of the first support rod and the second support rod; and the direction of extent of the transverse rod runs orthogonal to at least one of the first support rod and the second support rod.

12. An assortment comprising: a connector according to claim 1 and at least two transverse rods with at least one of different lengths and different transverse dimensions.

13. An assortment, according to claim 12, comprising at least one connector, wherein at least two couplings that are assigned to one or two connectors have clamping regions designed to clamp support rods with different transverse dimensions.

14. The assortment, according to claim 13, comprising at least two connectors.

15. The connector according to claim 1, wherein the connector is made of biocompatible material.

16. A spinal column support device, comprising: two support rods; and a connector according to claim 1 that connects said support rods.

\* \* \* \* \*